(12) United States Patent
Abdel-Monem et al.

(10) Patent No.: US 8,119,836 B2
(45) Date of Patent: *Feb. 21, 2012

(54) DERIVATIVES OF SELENO-AMINO ACIDS

(75) Inventors: Mahmoud M. Abdel-Monem, Oak Harbor, WA (US); Michael D. Anderson, Eden Prairie, MN (US)

(73) Assignee: Zinpro Corporation, Eden Prairie, MN (US)

( * ) Notice: Subject to any disclaimer, the term of this patent is extended or adjusted under 35 U.S.C. 154(b) by 374 days.

This patent is subject to a terminal disclaimer.

(21) Appl. No.: 12/436,325

(22) Filed: May 6, 2009

(65) Prior Publication Data

US 2009/0214697 A1    Aug. 27, 2009

Related U.S. Application Data

(62) Division of application No. 11/181,264, filed on Jul. 14, 2005, now Pat. No. 7,586,003.

(51) Int. Cl.
    *C07C 391/00*    (2006.01)
(52) U.S. Cl. .................................................... 562/559
(58) Field of Classification Search .................. None
    See application file for complete search history.

(56) References Cited

U.S. PATENT DOCUMENTS

| 5,552,440 A | 9/1996 | Crooks et al. |
| 6,911,550 B2 | 6/2005 | Abdel-Monem et al. |

FOREIGN PATENT DOCUMENTS

| CN | 1218043 A | 6/1999 |
| GB | 1518114 A | 7/1978 |
| JP | 60-190758 | 9/1985 |
| JP | 63-083061 | 4/1988 |

OTHER PUBLICATIONS

Blum, T., et al., "Synthesis of asymmetric [75Se]selenoethers via carbodiimides", J. of Labelled Compounds and Radiopharmaceuticals, 44(8):587-601 (2001).

Carland, M., et al., "Syntheses and structural studies of platinum(II) complexes of O-methylselenomethionine and related ligands", Inorganica Chimica ACTA, 359(10):3252-3256 (2006).

Chen, S. et al., "Preparation of [755e]-L-selenomethionine-sodium tetrahydroborate method", Yuanzineng Kexue Jishu, 20(2):136-141 (1986) Beijing, CH. Chemical Abstracts Service, Columbus, Ohio, US, 1987, XP002404495.

Cushman, D.W. et al., "Design of Poten Competitive Inhibitors of Angiotensin-Converting Enzyme. Carboxyalkanoyl and Mercaptoalkanoyl Amino Acids", 1977, Biochemistry, 16(25), 5484-5491.

Damico, R., "An Investigation of N-Substituted Methionine Derivatives for Food Supplementation", 1975, J. Agr. Food Chem., 23(1), 30-33.

Kornbrock, W., et al., "A New Efficient Synthesis of Acetyltelluro- and Acetylselenomethionine and Their Use in the Biosynthesis of Heavy-Atom Protein Analogs", 1996, J. Am. Chem. Soc., 118, 913-914.

Lee, J., et al., "Enantioseparation of chiral amino acids as the N(0,S)-ethoxycarbonylated diastereomeric esters by achiral dual-capillary column gas chromatography", the Analyst, 126(12):2128-2133 (2001).

Ogier, G., et al., "Contribution of 4-methylthio-2-oxobutanoate and its transaminase to the growth of methionine-dependent cells in culture: effect of transaminase inhibitors", Biochemical Pharmacology, 45(8):1631-1644 (1993).

Ritchey, J.A., et al., "Experimental and theoretical evidence fo cyclic selenurane formation during selenomethionine oxidation", Organic and Biomolecular Chemistry, 3(25):4337-4342 (2005).

Schmaljohann, J., "Polymer-supported synthesis of unsymmetrical n. c.a. [73,75Se]selenoethers by labeling of amino acids", Berichte des Forschungszentrum Juelich, vol. Juel-3108, pp. 1-136, 1995, Juelich, DE. Chemical Abstracts Service, Columbus, Ohio, US, 1995, XP002404494.

Schrauzer, G.N., "Nutritional selenium supplements: product types, quality, and safety", J. of the American College of Nutrition, 20(1):1-4 (2001).

Silverman, R.B., "The Organic Chemistry of Drug Design and Drug Action", 1992, Academic Press, p. 19.

*Primary Examiner* — Daniel Sullivan
*Assistant Examiner* — Yevegeny Valenrod
(74) *Attorney, Agent, or Firm* — McKee, Voorhees & Sease, P.L.C.

(57) ABSTRACT

Derivatives of seleno-alpha amino acids, particularly selenomethionine as enhanced bioavailable sources of selenium in animal diets.

5 Claims, No Drawings

DERIVATIVES OF SELENO-AMINO ACIDS

CROSS-REFERENCE TO RELATED APPLICATIONS

This is a Divisional Application of U.S. application Ser. No. 11/181,264 filed Jul. 14, 2005 which is hereby incorporated by reference in its entirety.

BACKGROUND OF THE INVENTION

The essential role of selenium in nutrition was first recognized by Schwarz and Foltz in 1957 (Schwarz, K. and Foltz, C. M., *Selenium as an integral part of factor 3 against dietary necrotic liver degeneration. J. Am. Chem. Soc.* 79:3292 (1957)). These researchers observed that rats developed liver necrosis when fed a purified diet deficient in vitamin E. However, the addition of selenium to the diet prevented the development of this condition. The ability of dietary selenium to prevent the development of exudative diathesis, a condition characterized by leakage of plasma into subcutaneous spaces of the abdomen and breast in chicken, was reported in the same year by Patterson et al (Patterson, E. L., Milstrey, R., Stokstad, E. L. R. *Effect of selenium in preventing exudative diathesis in chicks. Proc. Soc. Exp. Biol. Med.* 95: 617-620 (1957)). The important role of selenium in nutrition was further demonstrated by recognizing the practical effect of selenium deficiency in livestock (Muth, O. H., Oldfield, J. E., Remmert, L. F., and Schubert, J. R. *Effects of selenium and vitamin E on white muscle disease. Science* 128: 1090 (1958) and Hartley, W. J., and Grant, A. B. *A review of selenium responsive diseases of New Zealand livestock. Fed. Proc.* 2o: 679 (1961)). Subsequent work confirmed that selenium is an essential element for animals and that its deficiency results in various disorders (Combs, G. F. Jr., Combs, S. B. *The role of selenium in nutrition.* Academic Press, Orlando, Fla., pp 265-399 (1986b)).

The importance of selenium in human nutrition and the effects of its deficiency on human health were not recognized until the 1970s. Selenium deficiency was found to be one of the factors responsible for the Keshan disease, a human condition characterized by a dilated cardiomyopathy that affects persons living in rural areas of China. The incidence of the Keshan disease matched the distribution of selenium-deficient areas (*Keshan Disease Research Group of the Chinese Academy of Medical Sciences. Epidemiologic studies on the etiologic relationship of selenium and Keshan disease. Chin. Med J.* 92:477-482 (1979)). Furthermore, a prospective placebo-controlled study demonstrated that new cases of the disease can be prevented by the administration of sodium selenite tablets (*Keshan Disease Research Group of the Chinese Academy of Medical Sciences. Observations on effect of sodium selenite in prevention of Keshan disease. Chin. Med J.* 92:471-477 (1979)). The detrimental effects of diet-induced selenium deficiency in critically ill patients were reported in several case studies. Skeletal myopathy developed in one patient on total parenteral nutrition and was reversed by intravenous administration of selenomethionine (van Rij, A. M., Thomson, C. D., McKenzie, J. M., Robinson, M. F. *Selenium deficiency in total parenteral nutrition. Am. J. Clin. Nutr.* 32: 2076-2085 (1979)). Fatal cardiomyopathy induced by nutritional selenium deficiency was reported in a 43-year-old man receiving parenteral alimentation for 2 years before his death (Johnson, R. A., Baker, S. S., Fallon, J. T., Maynard, E. P., Ruskin, J. N., Wen, Z., Ge, K., and Cohen, H. J. *An occidental case of cardiomyopathy and selenium deficiency. The New England Journal of Medicine.* 304: 1210-1212 (1981)). In 1982, a second case of fatal cardiomyopathy associated with dietary selenium deficiency was reported in a patient on home parenteral nutrition for at least two years (*Selenium Deficiency and Fatal Cardiomyopathy in a Patient on Home Parenteral Nutrition. Gastroenterology.* 83:689-693 (1982)).

The recognition of the essential role of selenium in human and animal nutrition has resulted in the establishment of a Recommended Daily Allowance (RDA) for humans and approval of the inclusion of additional selenium compounds in animal feed. Recently, the Food and Nutrition Board of the Institute of Medicine revised the RDA for selenium to 55 µg (*Dietary Reference Intakes for Vitamin C, Vitamin E, Selenium, and Carotenoids.* Washington, D.C.: National Academy Press, (2000)). In 1974, the Food and Drug Administration (FDA) approved sodium selenite and sodium selenate as feed additive. These inorganic selenium salts can be added at the level of 0.3 ppm Se in feed dry matter. In June 2000, the FDA approved the use of selenium yeast in poultry broiler and layer diets.

The biochemical mechanism involved in manifesting the beneficial effects of selenium began to emerge in 1973 when selenium was found to be an essential component of the antioxidant enzyme glutathione peroxidase (Rotruck, J. T., Pope, A. L., Ganther, H. E., Swanson, A. B., Hafeman, D. G. F., and Hockstra, W. G. Selenium: *Biochemical Role as a Component of Glutathione Peroxidase. Science,* 179: 588-590 (1973) and Flohe, L., Gunzler, W. A. and Shock, H. H. *Glutathione Peroxidase. A Selenoenzyme. FEBS Lett.* 32: 132-134)). Concurrently, an extra cellular selenoprotein (Selenoprotein P) was discovered in rat, rhesus monkey and human plasma and found to be different than glutathione peroxidase (Moschos M. P. Selenoprotein P. *Cellular and Molecular Life Sciences.* 57: 1836-1845 (2000)). Another function of selenium is as a catalytically active component of the iodothyronine deiodinase enzymes that regulates thyroid hormone metabolism. More recently, selenocysteine was identified in the active center of thioredoxin reductase demonstrating the role selenium plays in various metabolic processes catalyzed by these enzymes.

Recent studies have shown that the role of selenium in mammalians is not limited to the physiological functions of selenoenzymes. It now appears that selenium has a very specific role in spermatogenesis that is essential for male fertility (Ursini F., Heim S., Kiess M., Maiorino M., Roveri A., Wissing J., Flohe' L. *Dual Function of the Selenoprotein PHGPx During Sperm Maturation. Science* 285: 1393-1396 (1999)). The identification of a specific selenoenzyme in the sperm nuclei further underscored the important role selenium plays in sperm maturation (Pfeifer H., Conrad M., Roethein D., Kyriakopoulos A., Brielmeier M., Bornkamm G. W., Behne D. *Identification of a Specific Sperm Nuclei Selenoenzyme Necessary for Protamine Thiol Cross-Linking During Sperm Maturation. FASEB J* 15: 1236-1238 (2001)).

The dietary requirements for selenium are usually fulfilled by the ingestion of diets containing naturally occurring organic selenium compounds. Food and feed ingredients rich in organic selenium compounds include meat, fish, dairy products, some vegetables and grains. The concentration of selenium in materials of plant origin often depends on the concentration of selenium in the soil where the plants were grown. The soil of the Rocky Mountain States contains higher levels of selenium than other states and plants growing on these soils contain higher levels of selenium. The majority of organic selenium in natural food and feed ingredients is present as L-selenomethionine. Some accumulator plants and vegetables such as garlic, onions and broccoli growing on selenium rich soils contain Se-methylselenocysteine and its derivatives as the major organic selenium compounds. One of the predominant forms of selenium in native forage plants of the U.S. is selenate. Of 24 plants studied, selenate represented 5-92% of total selenium. Selenite was absent in all but one of these plants which contained 3% of total selenium as selenite. (Whanger P. D. *Selenocompounds in Plants and Animals and their Biological Significance. Journal of the American College of Nutrition*, 12: 223-232 (2002)). Regardless of the form in which the selenium is ingested, it is transformed by a variety of metabolic pathways via the same intermediary pool into the specific selenocysteine-containing selenoproteins which are responsible for selenium biological effects. The levels of these selenocysteine-containing selenoproteins in tissues appear to be homeostatically controlled. Ingestion of supplemental selenium above the optimal requirements does not appear to increase the concentrations of the specific selenoproteins in tissues. However, ingestion of selenomethionine results in higher retention of selenium in tissues than those observed with other sources of selenium. This is attributed to the fact that only a fraction of selenomethionine is metabolized similar to other sources of selenium via the intermediary pool to specific selenocysteine-containing proteins. A certain percentage of ingested selenomethionine is incorporated non-specifically directly into proteins in place of methionine. This non-specifically bound selenium is present in high concentrations in methionine rich proteins. The fraction of ingested selenomethione that is incorporated in non-specific proteins appears to be dependent on the ratio of selenomethionine to methionine and not selenium status. When low methionine diets are ingested, the increased non-specific incorporation of selenomethionine in proteins resulted in the decreased concentrations and effects of the specific selenoproteins. Non-specific incorporation of selenomethionine takes place in the proteins of skeletal muscles, erythrocytes, pancreas, liver, stomach, kidneys and the gastrointestinal mucosa. The release of selenomethionine from body proteins is linked to protein turnover. A steady state concentration of selenomethionine in tissues may be established if the intake of the seleno-amino acid is maintained over extended period of time. (Schrauzer G. N. *Nutritional Selenium Supplements: Product Types, Quality, and Safety. Journal of the American College of Nutrition*, 20: 1-4 (2001)).

The disposition of selenomethionine, Se-methyl-selenocysteine, selenite, and selenate in animals has been carefully studied. These common sources of selenium in animal nutrition take different pathways to the intermediary selenium pool which is ultimately incorporated in the specific selenoproteins or further converted into polar metabolites that can be readily excreted.

A fraction of the ingested selenium source is eliminated via a number of pathways. Some of orally ingested selenite and selenate is reduced in the gastrointestinal tract to elemental selenium which is excreted in feces. Selenite and selenate are also excreted in urine.

Supplementation of animal feed with an approved source of selenium is gaining popularity. Currently, inorganic sources such as selenite and selenate as well as the organic source selenium yeast are approved by the FDA as feed ingredients. However, the amount of selenium that can be added and the species of livestock that may be supplemented are regulated. The approval of the use of the inorganic sources of selenium such as selenite and selenate as feed ingredients is curious since these do not occur naturally in significant concentrations in feed. L-Selenomethionine is the form of selenium most commonly present in natural foods and feed. However, synthetic L-selenomethionine has not been commercially available at reasonable prices for use as feed ingredient in livestock production. Therefore, selenium enriched yeast has been used as a practical affordable source of L-selenomethionine. Special strains of *Saccharomyces cerevisiea* grown in a selenium rich medium accumulate as much as 3000 µg Se per g dry matter. Most of the selenium in yeast exists as L-selenomethionine. The L-selenomethionine is present primarily incorporated in the yeast protein in place of L-methionine. Other organic selenium compounds may be present in low concentrations including Se-adenosyl-selenohomocysteine (2-5%), selencysteine (0.5%), methylselenocysteine (0.5%), selenocystathionine (0.5%), and γ-glutamyl-Se-methylselenocysteine (0.5%). Only traces of inorganic selenium may be present in the yeast as selenite or selenate (Schrauzer G. N. *Selenomethionine: A Review of its Nutritional Significance, Metabolism and Toxicity. J. Nutr.* 130: 1653-1656 (2000)).

Several studies were published during the last several years comparing the effects of selenite and selenium yeast supplements on the selenium status and health of livestock. In selenium deficient animals, the selenium concentrations in plasma and tissues increase linearly as intake of selenium increases to a point after which plasma and tissue selenium concentrations do not change significantly with increased intake. For example the relationship of dietary selenium from sodium selenite to selenium concentrations in plasma and milk in dairy cows was examined by Maus et al. Selenium concentration in plasma and milk increased linearly as intake of selenium increased from about 2-6 mg/day. Further increases in intake resulted in only little change in plasma and milk selenium (Maus R. W., Martz F. A., Belyea R. L. and Weiss M. F., *Relationship of Dietary Selenium to Selenium in Plasma and Milk from Dairy Cows, J Dairy Sci*, 63: 532-537 (1980)).

Selenium was found to be more bioavailable from selenium yeast than from selenite or selenate in several animal studies. The increase in tissue selenium concentration was greater in animals fed selenium yeast compared to animals fed selenite. However, the increase in glutathione peroxidase activity was about the same regardless of the source of supplemental selenium. The favorable effects of selenium supplementation on animal health were demonstrated in several studies. For example, selenium supplementation improved udder health in dairy cows as demonstrated by a decrease in the percent quarters harboring mastitis pathogens and a decrease in somatic cells count in milk. Again the effects of selenium yeast were greater than those of sodium selenite (Malbe M., Klassen M., Fang W., Mylls V., Vikerpuur M., Nyholm K, Sankari S., Sourta K., and Sandholm M. *Comparisons of Selenite and Selenium Yeast Feed Supplements on Se-incorporation, Mastitis and Leucocyte Function in Se-deficient Dairy Cows, J Vet Med A,* 42: 111-121 (1995)).

In summary, it is now well established that dietary selenium is essential for the health and wellbeing of humans and animals. Several studies have demonstrated that selenium is more bioavailable from organic sources than from inorganic sources. The only organic selenium source available for commercial use is selenium rich yeast preparation. In yeast, selenium exists primarily as L-selenomethionine rich proteins. Although Selenium yeast is now widely accepted as a source of dietary selenium, its use suffers from several shortcomings. The concentration of organically bound selenium in yeast is limited by its ability to form L-selenomethionine from the selenite enriched media. Currently, the highest possible concentration of selenium in yeast appears to be 2000 µg/g dry matter. Secondly, since the organically bound selenium in yeast is produced by a biological process that is vulnerable to subtle variations in the large scale production process, the exact composition of the selenium compounds is variable and is not readily known. Occasionally, yeast contains variable concentrations of inorganic selenium compounds such as selenites and selenates. Thirdly, the organic selenium compounds are present in yeast as part of the intracellular proteins. Before these compounds are available for absorption after being ingested, the cell walls of yeast must rupture to release the protein into the animals' gastrointestinal tract where it can be subjected to the proteolytic effects of digestive enzymes. It is only after the protein is hydrolyzed to single amino acids or dipeptides that the selenium compounds can be absorbed. The release of the selenium compounds as single amino acids or dipeptides from the intact yeast cells is not complete and is highly dependent on the conditions in the gastrointestinal tract. Because of these shortcomings, there is important need to develop alternatives to selenium enriched yeast to serve as a readily bioavailable dietary source of selenium. Our earlier patent, U.S. Pat. No. 6,911,550, related to complex salts. This improvement relates to certain esters and organic derivatives that are very stable.

Recently, the demand for a dietary sources of selenium with improved bioavailability for use as a supplement for human and livestock has increased. Synthetic seleno-amino acids have recently become commercially available at a reasonable cost. These amino acids however have low water solubility and their crystals have water repellent properties that result in low rate of dissolution. Low solubility and slow rate of dissolution lower the bioavailability of these compounds after feeding to animals. One primary objective of this invention is to identify derivatives of seleno-amino acids with improved bioavailability and then prepare them.

Selenium like sulfur, is a member of group VIA elements. It exists in different allotropic forms and has oxidation states of −2, 0, +2, +4, and +6. Selenium is a nonmetallic element. It can form mono-atomic anions and therefore can form ionic as well as covalent bonds. In the oxidation state −2, selenium forms covalent bonds with carbon substituents and can often replace sulfur in naturally occurring compounds. The biological role of selenium is attributed to these naturally occurring compounds in which selenium exists in the −2 oxidation state and is covalently bound, usually with carbon as part of functional proteins. Seleno-amino acids have been proposed as dietary sources of selenium. However, it is recognized that the bioavailability of these compounds may be significantly diminished by the nutritional status of the animal and the composition of the diet and gastrointestinal tract contents. Therefore it was desirable to explore derivatives of the seleno-amino acids that may improve the bioavailability of these amino acids. In a previous patent (U.S. Pat. No. 6,911,550) the inventors of the present application described reversible derivatives of seleno amino acids with improved bioavailability. These reversible derivatives are 1:1 zinc complexes of selenoamino acids such as L-selenomethionine. The primary object of the present invention is to make novel irreversible derivatives of seleno-amino acids with improved bioavailability. These novel compounds are formed by chemically modifying the selenoamino acids by forming covalent bonds between the α-amino and/or the carboxyl group and a protective group. These chemically stable compounds are enzymatically modified to the selenoamino acid after being ingested by the animal.

Another object of the invention is to describe methods of preparation of these derivatives and their use as feed ingredients in livestock.

SUMMARY OF THE INVENTION

Novel derivatives of seleno-amino acids that are effective dietary sources of supplemental selenium in humans and livestock are prepared. The novel derivatives have improved physical, chemical or biological properties over the parent seleno-amino acid. These derivatives possess enhanced bioavailability and/or increased stability of the seleno-amino acids. They are 1:1 complexes of seleno-amino acids such as L-selenomethionine.

DETAILED DESCRIPTION OF A PREFERRED EMBODIMENT

Because of unsatisfactory performance of presently available selenium sources for use in feed supplements, it was necessary then to explore derivatives of selenomethionine that have improved bioavailability. The desired properties of the novel derivatives include:
1. The derivative must be a readily bioavailable source of selenium.
2. The derivative must be more stable than the parent compound.
3. The physical properties of the derivative such as solubility, rate of dissolution, odor are more favorable than the parent compound.
4. The derivative can be easily prepared from the parent compounds by using commercially available reagents and at a reasonable cost.
5. The derivative must be as safe as the parent compound recognizing that all selenium containing compounds have a narrow range of safety.
6. The derivative must be stable in the content of the rumen so it can be used as a source of selenium in rumenat animals.

Other commercially available seleno-amino acids such as methyl-L-selenocysteine, were found to posses similar undesirable physical properties as L-selenomethionine. Therefore, derivatives of these selenoamino acids were also prepared. These derivatives were found to have similar properties as those of selenomethionine.

One group of seleno-amino acid derivatives is the simple aliphatic esters such as methyl-, ethyl-, propyl-, and isopropyl esters. Among this group the isopropyl esters were the preferred compounds. These are readily prepared by the reaction of the seleno-amino acid with isopropyl alcohol in the presence of the appropriate catalyst or coupling agents. These included concentrated sulfuric acid and thionyl chloride. The amino acid ester is usually separated as the hydrochloride salt. The L-Selenomethionine Isopropyl Ester Hydrochloride is a readily soluble in water, and is significantly more stable than L-selenomethionine in the solid state and in solution. These derivatives have much greater lipid solubility than the parent seleno-amino acids and will be rapidly absorbed by passive diffusion from intestinal contents at pH>5.0.

The second group of derivatives explored is the N-Succinyl derivatives of seleno-amino acids. These compounds were readily obtained by the reaction of the seleno-amino acids with succinic anhydride. These compounds are partially dissociated acids because the α-amino group of the seleno-amino acid is masked. These compounds are separated and easily purified as their salts. The potassium, sodium, calcium or magnesium salts may be prepared. The Sodium salt of N-Succinyl L-Selenomethione is readily soluble in water. It is significantly more stable than L-Selenomethionine in the solid state and in solution. These derivatives have much greater lipid solubility than the parent seleno-amino acids and will be rapidly absorbed by passive diffusion from gastro-intestinal contents at pH<3.0.

The third group of derivatives explored is the N-Carbamoyl and Hydantoin derivatives of seleno-amino acids. N-Carbamoyl L-Selenomethionine is obtained by the reaction between L-Selenomethionine and Potassium Cyanate in aqueous solution at 90° C. Heating the N-Carbamoyl derivative in 3 N hydrochloric acid provide L-Selenomethionine Hydantoin. The N-carbamoyl derivative is more soluble in water and the solution appears to be more stable than the parent seleno-amino acid. The Hydantoin is less soluble and appears to be more stable than the parent seleno-amino acid.

The compounds described above are reversible derivatives of the seleno-amino acids. After ingestion by the animal, they are expected to be readily converted to the parent seleno-amino acids primarily by enzyme catalyzed reactions. For example, The L-selenomethionine isopropyl ester is expected to be readily hydrolyzed by esterases present in the blood and other tissues such as the liver. The non-enzymatic hydrolysis of esters at pH 7.4 of the plasma is also possible. The N-Succinyl derivatives are likely to be enzymatically hydrolyzed by amidases in plasma and liver.

The seleno-amino acid derivatives described in this invention may be added to solid or liquid feed as a readily available source of selenium. The amount of the compound added will depend on the animal being supplemented. For swine and poultry, the diet will be supplemented by 0.05-2.00 ppm Se, preferably 0.1-0.3 ppm Se. For cattle, the feed will be supplemented by 0.05-10 mg Se per head per day, preferably 2-7 mg Se per head per day.

The following examples are offered to illustrate the practical methods of obtaining these complexes, their properties, and their use as sources of selenium in animal nutrition.

EXAMPLE 1

Preparation of L-Selenomethionine Isopropyl Ester Hydrochloride (Compound 1)

In a 1000-ml round bottom flask was added isopropyl alcohol (150 ml). The flask was placed in an ice-water bath and concentrated sulfuric acid (43.208 g of Technical grade minimum 93%) was carefully added dropwise with constant agitation. L-Selenomethionine (66.962 g, 0.338 moles) was carefully added with continued agitation. A Soxhlet extraction tube was attached to the top of the flask. A glass extraction thimble with a fritted disc is filled with Molecular Sieves 3A was placed in the extraction tube. Isopropyl alcohol was added to fill the extraction tube. A reflux condenser was attached to the extraction tube. The mixture is heated by a heating mantle to cause gentle reflux of the isopropyl alcohol. The reaction mixture was heated under reflux for 48 hrs. The heating was discontinued and the flask was placed in an ice-water bath. Ammonium hydroxide solution is added slowly with continued mixing. A voluminous white precipitate was formed. The mixture was filtered and the precipitate is washed with isopropyl alcohol. The combined filtrate and washings were concentrated under reduced pressure to give a thick oil. The residue was dissolved in 100-ml of ethyl acetate. The ethyl acetate solution was transferred into a separatory funnel and extracted with successive portions of dilute ammonium hydroxide solution and Brine solution. The ethyl acetate extract was dried over anhydrous magnesium sulfate, filtered and the solvent removed under reduced pressure to give a thick yellow oil (42.337 g, 52.61% yield). The oil was dissolved in isopropyl alcohol (200 ml) and concentrated hydrochloric acid (20 g) was added. The mixture was concentrated under reduced pressure the residue was dissolved in the minimum amount of ethyl acetate. Dry ether was added dropwise until turbidity appeared. The mixture was stored in a refrigerator for 4 days. A white crystalline precipitate was filtered and washed with dry ether.

The FTIR spectrum of the solid in a potassium bromide pellet showed absorption peaks at about: 3413.8(W), 2981.7 (vs), 2877.6(vs), 2615.3(m), 2488.0(w), 2100.0(m), 1732.0 (vs), 1585.4(m), 1512.1(m), 1465.8(m), 1442.7(m), 1377.1 (m), 1276.8(s), 1242.1(vs), 1188.1(s), 1107.1(vs), 1068.5(m), 902.6(m) and 813.9(w) $cm^{-1}$. (w, weak; m, medium; s, strong; vs, very strong). This spectrum is different than that of L-selenomethionine which showed absorption peaks at about: 3433.1(w), 2923.9(s), 2731.0(m), 2611.4(m), 2117.7(w), 1608.5(s), 1581.5(vs), 1512.1(s), 1411.8(s), 1338.5(m), 1269.1(w), 1218.9(w), 1153.4(w), and 540.0(w) $cm^{-1}$.

A solution containing 1 mg/ml of L-selenomethionine isopropyl ester hydrochloride in water was analyzed by HPLC using a UV/Vis detector at 210 nm and 20 μl of the sample was injected onto the column by using a Rheodyne Loop injector. A 250×4.6 mm Discovery Cyano column (Supelco) was used with 0.1% Acetic Acid at 1 ml/min as the mobile phase. L-Selenomethionine isopropyl ester hydrochloride had a retention time of 4.467 min. L-Selenomethionine has a retention time of 4.167 min in this system. A single peak accounting for over 99% of detector response was obtained with the L-selenomethionine isopropyl ester hydrochloride. This system was useful for the determination of L-selenomethionine isopropyl ester hydrochloride in premixes.

EXAMPLE 2

Preparation of N-Succinyl L-Selenomethionine (Compound 2)

A 3-neck 250-ml round bottom flask was equipped with a thermometer, a reflux condenser and an addition funnel. Ethyl acetate (75 ml) was placed into the flask. Succinic anhydride (12.404 g) was finely pulverized in a mortar and added to the ethyl acetate in the flask. The mixture was stirred by a magnetic stirrer until all solids dissolved. L-Selenomethionine (19.630 g, 0.1 mole) was added. Dilute sulfuric acid (1.0 ml of a solution obtained by diluting 1 part concentrated sulfuric acid with 5 parts water). The mixture was heated under reflux with continued stirring for 1 hr. The hot clear solution was filtered. A white crystalline precipitate was formed as the filtrate was cooled. The precipitate weighed 24.92 g (84.14% yield).

The FTIR spectrum of the finely ground crystals obtained above in a potassium bromide pellet showed absorption peaks at about: 3313.5(m), 3091.7(w), 2931.6(m), 2626.9(w), 1714.6(vs), 1647.1(s), 1616.2(m), 1434.9(m), 1409.9(m), 1245.9(s), 1195.8(s), 964.3(w), 704.0(w), and 636.5(w) $cm^{-1}$. (w, weak; m, medium; s, strong; vs, very strong). This spectrum is different than that of L-selenomethionine which showed absorption peaks at about: 3433.1(w), 2923.9(s), 2731.0(m), 2611.4(m), 2117.7(w), 1608.5(s), 1581.5(vs), 1512.1(s), 1411.8(s), 1338.5(m), 1269.1(w), 1218.9(w), 1153.4(w), and 540.0(w) $cm^{-1}$.

A solution containing 1 mg/ml of N-Succinyl L-selenomethionine in water was analyzed by HPLC using a UV/Vis detector at 210 nm and 20 μl of the sample was injected onto the column by using a Rheodyne Loop injector. A 250×4.6 mm Discovery Cyano column (Supelco) was used with 0.1% Acetic Acid at 1 ml/min as the mobile phase. The N-succinyl L-Selenomethionine had a retention time of 5.56 min. L-Selenomethionine has a retention time of 4.167 min in this system. A single peak accounting for over 99.54% of detector response was obtained with the N-succinyl L-selenomethionine. This system was useful for the determination of N-succinyl L-selenomethionine in premixes.

EXAMPLE 3

Preparation of N-Carbamoyl L-Selenomethionine (Compound 3)

A 3-neck 250-ml round bottom flask was equipped with a thermometer, a reflux condenser and an addition funnel. Water (40 ml) was placed into the flask. Potassium cyanate (9.735 g, 0.115 moles) was added to the water in the flask and the cold mixture was stirred by a magnetic stirrer until all solids dissolved. L-Selenomethionine (19.815 g, 0.1 moles) was added. The mixture was heated under reflux with vigorous stirring. The inside temperature reached 94° C. and then lowered to 80-85° C. The reaction mixture was maintained at 80-85° C. for 2 hrs. The clear solution obtained was cooled to room temperature. Hydrochloric acid (11.272 g, 0.115 moles) was added slowly with continued stirring. A heavy white crystalline precipitate was formed and filtered under reduced pressure. The precipitate weighed 20 g (83.65% yield).

The FTIR spectrum of the finely ground crystals obtained above in a potassium bromide pellet showed absorption peaks at about: 3458.1(s), 3303.8(m), 2929.7(w), 1685.7(vs), 1631.7(vs), 1560.3(vs), 1442.7(w), 1411.8(w), 1282.6(s), 1244.0(w), 1197.7(w), 1180.4(w), 1103.2(w), 931.6(w), 775.3(w), 719.4(w), 576.7(w) and 478.3(w) cm$^{-1}$. (w, weak; m, medium; s, strong; vs, very strong). This spectrum is different than that of L-selenomethionine which showed absorption peaks at about: 3433.1(w), 2923.9(s), 2731.0(m), 2611.4(m), 2117.7(w), 1608.5(s), 1581.5(vs), 1512.1(s), 1411.8(s), 1338.5(m), 1269.1(w), 1218.9(w), 1153.4(w), and 540.0(w) cm$^{-1}$.

A solution containing 1 mg/ml of N-Carbamoyl L-selenomethionine in water was analyzed by HPLC using a UV/Vis detector at 210 nm and 20 μl of the sample was injected onto the column by using a Rheodyne Loop injector. A 250×4.6 mm Discovery Cyano column (Supelco) was used with 0.1% Acetic Acid at 1 ml/min as the mobile phase. The N-carbamoyl L-Selenomethionine had a single peak accounting for over 99.54% of detector response and a retention time of 5.15 min. L-Selenomethionine has a retention time of 4.167 min in this system. This system was useful for the determination of N-carbamoyl L-selenomethionine in premixes.

EXAMPLE 4

Preparation of L-Selenomethionine Hydantoin (Compound 4)

A 3-neck 250-ml round bottom flask was equipped with a thermometer, a reflux condenser and an addition funnel. Water (40 ml) was placed into the flask. N-Carbamoyl L-selenomethionine (11.969 g, 0.05 moles) was added to the water in the flask and the mixture was stirred by a magnetic stirrer with cooling. Hydrochloric acid (14.599 g, 0.15 moles) was added slowly. The mixture was heated under reflux with vigorous stirring for 2 hrs. The clear solution was filtered while hot and then cooled to room temperature. A heavy white crystalline precipitate was formed and filtered under reduced pressure. The precipitate weighed 8.72 g (78.88% yield).

The FTIR spectrum of the finely ground crystals obtained above in a potassium bromide pellet showed absorption peaks at about: 3062.7(w), 2761.9(w), 1774.4(s), 1732.0(vs), 1423.4(m), 1265.2(w), 1203.5(w), 748.3(w), 632.6(w), and 455.2(w) cm$^{-1}$. (w, weak; m, medium; s, strong; vs, very strong). This spectrum is different than that of L-selenomethionine which showed absorption peaks at about: 3433.1(w), 2923.9(s), 2731.0(m), 2611.4(m), 2117.7(w), 1608.5(s), 1581.5(vs), 1512.1(s), 1411.8(s), 1338.5(m), 1269.1(w), 1218.9(w), 1153.4(w), and 540.0(w) cm$^{-1}$.

A solution containing 1 mg/ml of L-selenomethionine hydantoin in water was analyzed by HPLC using a UV/Vis detector at 210 nm and 20 μl of the sample was injected onto the column by using a Rheodyne Loop injector. A 250×4.6 mm Discovery Cyano column (Supelco) was used with 0.1% Acetic Acid at 1 ml/min as the mobile phase. The L-selenomethionine hydantoin showed a single peak accounting for over 99.72% of detector response and a retention time of 5.94 min. L-Selenomethionine has a retention time of 4.167 min in this system. This system was useful for the determination of L-selenomethionine hydantoin in premixes.

EXAMPLE 5

Comparison of the Effects of Sodium Selenite and N-Succinyl L-Selenomethionine (Compound 2) on Tissue Selenium Content and Whole-Blood Glutathione Peroxidase Activity of Lactating Cows Three premixes were prepared for use in a field study in lactating cows. One of the premixes contained no additional source of selenium and was intended to serve as the placebo. The second contained sodium selenite and the third contained N-Succinyl L-Selenomethionine (Compound 2). Each of the premixes was prepared by mixing an amount of the selenium source with sufficient amount of finely ground sugar to contain 250 ppm of selenium. Each premix was color identified by the incorporation of a solution of a food color during formulation and given a letter designation by random selection. The premixes were provided to the animal nutritionists blinded, i.e. they did not know the source of selenium in each of the premixes. This was done to avoid any possible biases in the interpretation of the results of the feeding experiments.

Thirty lactating cows were fed one of the three premixes as a daily topdress. The effect of these selenium sources on tissue selenium content and whole blood glutathione peroxidase activity were determined. All cows were fed a total mixed diet devoid of added selenium for an initial 8-week depletion period. Daily rations were topdressed with an amount of the premix to provide 7.5 mg selenium. Treatments were continued for 8-week followed by a 4-week depletion period. Milk samples were collected on one day per week beginning the week prior to the first depletion period (Week 0) and continuing through the 20 weeks of the experiment. The selenium content of the milk serum obtained after the samples were defatted was determined. The selenium concentrations in milk serum for weeks 0, 8, 12, 16, and 20 are reported in Table 1. Blood samples were collected on one day per week beginning the week prior to the first depletion period (Week 0) and at four week intervals throughout the experiment (Weeks 8, 12, 16 and 20 in Table 1). The blood samples were draw into trace-element free vacutainer tubes containing an anticoagulant. Aliquots of whole blood were analyzed for selenium and glutathione peroxidase activity. Other aliquots of blood were centrifuged to harvest plasma and the selenium content of the plasma samples was determined. Liver samples were obtained by biopsy on one day per week beginning the week prior to the first depletion period (Week 0) and at four week intervals throughout the experiment (Weeks 8, 12, 16 and 20 in Table 1). Liver samples were analyzed for selenium content. The results of the experiment are reported in Table 1. The results in Table 1 show that the selenium concentrations in milk serum, plasma and liver after 8 weeks of restriction of selenium intake (Wk 8) were significantly lower than those before the start of the depletion period (Wk 0). Feeding the cows a mixed diet that does not contain supplemental selenium (Placebo) results in small increases in the selenium concentrations but the basal level at Wk 0 were not fully restored. However, feeding a diet supplemented with either sodium selenite or N-Succinyl L-Selenomethionine (Compound 2) resulted in progressive and significant increases in the selenium concentrations in these tissues (Wk 12 & Wk 16). The concentrations of selenium decreased significantly in all tissues at the end of the second depletion period (Wk 20). The dramatic changes in the selenium concentrations in response to changes in dietary intake of selenium indicate that these tissues are sensitive indicators of the dietary selenium status of the lactating cows. It is important to note that Compound 2 caused statistically significant higher increases than sodium selenite in the selenium concentration of these three tissues indicating that N-Succinyl L-Selenomethionine is a more bioavailable source of dietary selenium than sodium selenite.

The changes in the selenium concentration and glutathione peroxidase activity (GPX) in whole blood in response to changing dietary selenium intake were less sensitive than those in milk serum, plasma and liver. This indicates that these parameters are not useful indicators of the selenium status of lactating cows.

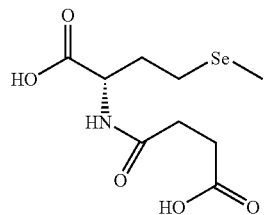

(S)-4-(1-carboxy-3-(methylselanyl)propylamino)-4-oxobutanoic acid
N-Succinyl L-Selenomethionine Compound 3

N-Carbomoyl L-Selenomethionine

Compound 4

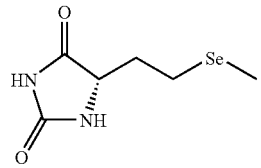

(S)-5-(2-(methylselanyl)ethyl)imidazolidine-2,4-dione
L-Selenomethionine hydantoin As used herein the term "biologically active derivatives" means organic covalently bound compounds prepared from the basic structure (for example L-selenomethionine) that retains the bioavailability properties to provide selenium diet enrichment of animals.

From the above written description and examples 1-5 it can be seen that the invention accomplishes the primary objectives of the inventors. It should be noted these examples are illustrative and not to be taken as limiting, as the scope of the inventors are defined by the following claims.

What is claimed is:

1. A dietary supplement premix comprising:
an animal feed premix carrier and a compound selected from the group consisting of N-Succinyl L-Selenomethionine or salts thereof, N-Carbamoyl L-Selenomethionine or salts thereof, L-Selenomethionine Hydantoin and salts thereof in an amount sufficient to provide a selenium level per animal of from about 0.05 ppm to about 2.0 ppm.

TABLE 1

| Tissue | Compound | Wk 0 | Wk 8 | Wk 12 | Wk 16 | Wk 20 |
|---|---|---|---|---|---|---|
| Milk Serum Se (ng/ml) | Placebo | 13.55 | 4.37 | 9.27 | 7.26 | 10.94 |
| | Sodium Selenite | 13.01 | 3.89 | 11.93 | 22.84 | 10.94 |
| | Compound 2 | 14.96 | 4.30 | 25.18 | 30.37 | 10.91 |
| Plasma Se (ng/ml) | Placebo | 72.1 | 47.1 | 31.3 | 28.9 | 42.7 |
| | Sodium Selenite | 75.4 | 45.3 | 56.3 | 56.8 | 48.4 |
| | Compound 2 | 63.5 | 43.6 | 60.3 | 65.7 | 52.2 |
| Liver Se (ng/g dry wt.) | Placebo | 1231 | 793 | 672 | 660 | 677 |
| | Sodium Selenite | 1446 | 1034 | 1129 | 1185 | 934 |
| | Compound 2 | 1151 | 690 | 1437 | 1705 | 1003 |
| Whole Blood Se (ng/ml) | Placebo | 133.3 | 145.9 | 99.0 | 92.6 | 81.4 |
| | Sodium Selenite | 147.4 | 135.7 | 113.2 | 119.1 | 104.4 |
| | Compound 2 | 144.0 | 136.3 | 139.0 | 136.8 | 112.1 |
| Whole Blood GPX (EU/ml) | Placebo | 17.3 | 19.0 | 17.1 | 14.0 | 15.0 |
| | Sodium Selenite | 17.3 | 17.9 | 17.6 | 16.1 | 17.9 |
| | Compound 2 | 18.2 | 19.2 | 18.7 | 17.5 | 19.8 |

Compound 1

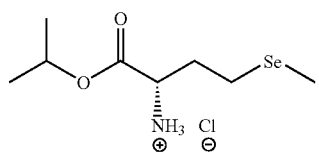

L-Selenomethionine Isopropyl Ester Hydrochloride

2. The dietary supplement of claim 1 wherein the amount of compound added to the pre-mix is sufficient to provide a selenium level per animal of from about 0.1 ppm to about 0.03 ppm.

3. A dietary supplement premix containing irreversible derivatives of the seleno alpha amino acid Selenomethionine, wherein the derivatives are $C_1$ to $C_3$ esters added to an animal feed premix in an amount sufficient to provide selenium levels in each animal at from about 0.05 ppm to about 2.0 ppm.

4. The dietary supplement of claim 3 wherein the ester is isopropyl.

5. A method of supplementing the diet of animals with selenium comprising adding to their animal feed a compound selected from the group consisting of N-Succinyl L-Selenomethionine or salts thereof, N-Carbamoyl Selenomethionine or salts thereof, L-Selenomethionine Hydantoin and salts thereof, and seleno alpha amino acid L-Selenomethionine $C_1$ to $C_3$ esters in an amount sufficient to provide selenium levels in each animal of from about 0.05 ppm to about 2.0 ppm.

* * * * *